US012644873B2

(12) United States Patent　　　　　(10) Patent No.:　US 12,644,873 B2

Nallaperumal　　　　　　　　　　　　(45) Date of Patent:　　Jun. 2, 2026

(54) METHOD TO SHOW TRUE INDOOR AIR QUALITY EXPERIENCED

(71) Applicant: KIDDE FIRE PROTECTION, LLC, Bradenton, FL (US)

(72) Inventor: Pirammanayagam Nallaperumal, Hyderabad (IN)

(73) Assignee: KIDDE FIRE PROTECTION, LLC, Bradenton, FL (US)

( * ) Notice: Subject to any disclaimer, the term of this patent is extended or adjusted under 35 U.S.C. 154(b) by 438 days.

(21) Appl. No.: 18/295,311

(22) Filed: Apr. 4, 2023

(65) Prior Publication Data

US 2023/0324355 A1　　Oct. 12, 2023

Related U.S. Application Data

(60) Provisional application No. 63/329,130, filed on Apr. 8, 2022.

(51) Int. Cl.
*G01N 33/00*　　　　(2006.01)
*F24F 11/52*　　　　(2018.01)
*F24F 11/63*　　　　(2018.01)
*F24F 110/50*　　　(2018.01)

(52) U.S. Cl.
CPC .......... *G01N 33/0062* (2013.01); *F24F 11/52* (2018.01); *F24F 11/63* (2018.01); *F24F 2110/50* (2018.01); *G01N 33/0068* (2024.05)

(58) Field of Classification Search
None
See application file for complete search history.

(56) References Cited

U.S. PATENT DOCUMENTS

| 2018/0004178 A1* | 1/2018 | Haines | ................. | G05B 19/048 |
| 2019/0004023 A1* | 1/2019 | Kelly | ....................... | G01D 3/08 |
| 2021/0116144 A1* | 4/2021 | Morgan | ................... | F24F 11/59 |
| 2024/0310066 A1* | 9/2024 | Beitelmal | ................ | F24F 11/63 |

FOREIGN PATENT DOCUMENTS

CN　　　　202562903 U　　11/2012

* cited by examiner

*Primary Examiner* — Lina Cordero

(74) *Attorney, Agent, or Firm* — CANTOR COLBURN LLP

(57) ABSTRACT

A method of tracking an indoor air quality (IAQ) level experienced by an individual including: detecting a first IAQ data set within a first room at a plurality of time increments using a first IAQ detector in the first room; determining a first IAQ health level for each of the plurality of time increments; detecting a second IAQ data set within a second room at the plurality of time increments using a second IAQ detector in the second room; determining a second IAQ health level for each of the plurality of time increments; detecting the individual being located within the first room during a first time period and within the second room during a second time period; and combining the first IAQ health level during the first time period and the second IAQ health level during the second time period into a true IAQ health level graph.

19 Claims, 2 Drawing Sheets

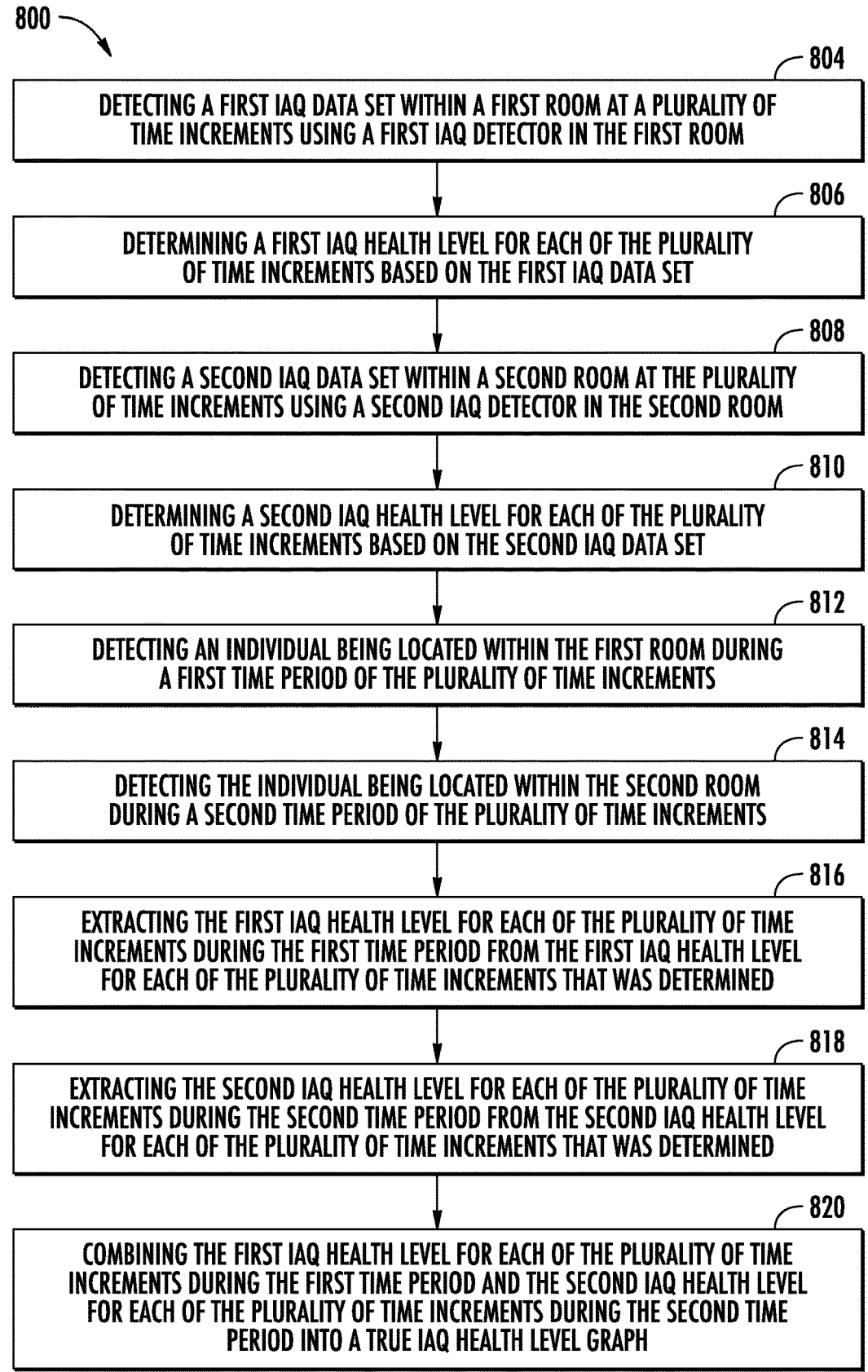

800 ⌐

804

DETECTING A FIRST IAQ DATA SET WITHIN A FIRST ROOM AT A PLURALITY OF
TIME INCREMENTS USING A FIRST IAQ DETECTOR IN THE FIRST ROOM

806

DETERMINING A FIRST IAQ HEALTH LEVEL FOR EACH OF THE PLURALITY
OF TIME INCREMENTS BASED ON THE FIRST IAQ DATA SET

808

DETECTING A SECOND IAQ DATA SET WITHIN A SECOND ROOM AT THE PLURALITY
OF TIME INCREMENTS USING A SECOND IAQ DETECTOR IN THE SECOND ROOM

810

DETERMINING A SECOND IAQ HEALTH LEVEL FOR EACH OF THE PLURALITY
OF TIME INCREMENTS BASED ON THE SECOND IAQ DATA SET

812

DETECTING AN INDIVIDUAL BEING LOCATED WITHIN THE FIRST ROOM DURING
A FIRST TIME PERIOD OF THE PLURALITY OF TIME INCREMENTS

814

DETECTING THE INDIVIDUAL BEING LOCATED WITHIN THE SECOND ROOM
DURING A SECOND TIME PERIOD OF THE PLURALITY OF TIME INCREMENTS

816

EXTRACTING THE FIRST IAQ HEALTH LEVEL FOR EACH OF THE PLURALITY OF TIME
INCREMENTS DURING THE FIRST TIME PERIOD FROM THE FIRST IAQ HEALTH LEVEL
FOR EACH OF THE PLURALITY OF TIME INCREMENTS THAT WAS DETERMINED

818

EXTRACTING THE SECOND IAQ HEALTH LEVEL FOR EACH OF THE PLURALITY OF TIME
INCREMENTS DURING THE SECOND TIME PERIOD FROM THE SECOND IAQ HEALTH LEVEL
FOR EACH OF THE PLURALITY OF TIME INCREMENTS THAT WAS DETERMINED

820

COMBINING THE FIRST IAQ HEALTH LEVEL FOR EACH OF THE PLURALITY OF TIME
INCREMENTS DURING THE FIRST TIME PERIOD AND THE SECOND IAQ HEALTH LEVEL
FOR EACH OF THE PLURALITY OF TIME INCREMENTS DURING THE SECOND TIME
PERIOD INTO A TRUE IAQ HEALTH LEVEL GRAPH

FIG. 2

METHOD TO SHOW TRUE INDOOR AIR QUALITY EXPERIENCED

CROSS-REFERENCE TO RELATED APPLICATIONS

This application claims the benefit of U.S. Provisional Application No. 63/329,130, filed Apr. 8, 2022, all of which are incorporated herein by reference in their entirety.

BACKGROUND

The embodiments herein generally relate to indoor air quality sensors and more specifically, a method and apparatus to display an indoor air quality detected by indoor air quality sensors.

Indoor air quality is an important factor to create a safer indoor living environment. Indoor air quality devices such as, air purifiers, air conditioners, humidifiers, dehumidifier, and ventilators are often used to control indoor air quality, but individuals are often given little feedback as to a resultant indoor air quality provided by these systems.

BRIEF DESCRIPTION

According to one embodiment, a method of tracking an indoor air quality (IAQ) level experienced by an individual is provided. The method including: detecting a first IAQ data set within a first room at a plurality of time increments using a first IAQ detector in the first room; determining a first IAQ health level for each of the plurality of time increments based on the first IAQ data set; detecting a second IAQ data set within a second room at the plurality of time increments using a second IAQ detector in the second room; determining a second IAQ health level for each of the plurality of time increments based on the second IAQ data set; detecting the individual being located within the first room during a first time period of the plurality of time increments; detecting the individual being located within the second room during a second time period of the plurality of time increments; extracting the first IAQ health level for each of the plurality of time increments during the first time period from the first IAQ health level for each of the plurality of time increments that was determined; extracting the second IAQ health level for each of the plurality of time increments during the second time period from the second IAQ health level for each of the plurality of time increments that was determined; and combining the first IAQ health level for each of the plurality of time increments during the first time period and the second IAQ health level for each of the plurality of time increments during the second time period into a true IAQ health level graph.

In addition to one or more of the features described above, or as an alternative, further embodiments may include displaying the true IAQ health level graph on a computing device of the individual.

In addition to one or more of the features described above, or as an alternative, further embodiments may include transmitting the true IAQ health level graph to the computing device of the individual.

In addition to one or more of the features described above, or as an alternative, further embodiments may include that detecting the individual being located within the first room during the first time period of the plurality of time increments further includes: detecting wireless advertisement of a computing device of the individual using the first IAQ detector.

In addition to one or more of the features described above, or as an alternative, further embodiments may include that the wireless advertisement is a Bluetooth signal.

In addition to one or more of the features described above, or as an alternative, further embodiments may include that the first IAQ detector is located in a fire detector.

According to another embodiment, an IAQ detector system having one or more IAQ detectors is provided. The IAQ detector system including: a processor; and a memory including computer-executable instructions that, when executed by the processor, cause the processor to perform operations. The operations including: detecting a first IAQ data set within a first room at a plurality of time increments using a first IAQ detector in the first room; determining a first IAQ health level for each of the plurality of time increments based on the first IAQ data set; detecting a second IAQ data set within a second room at the plurality of time increments using a second IAQ detector in the second room; determining a second IAQ health level for each of the plurality of time increments based on the second IAQ data set; detecting an individual being located within the first room during a first time period of the plurality of time increments; detecting the individual being located within the second room during a second time period of the plurality of time increments; and extracting the first IAQ health level for each of the plurality of time increments during the first time period from the first IAQ health level for each of the plurality of time increments that was determined; extracting the second IAQ health level for each of the plurality of time increments during the second time period from the second IAQ health level for each of the plurality of time increments that was determined; and combining the first IAQ health level for each of the plurality of time increments during the first time period and the second IAQ health level for each of the plurality of time increments during the second time period into a true IAQ health level graph.

In addition to one or more of the features described above, or as an alternative, further embodiments may include that the operations further include: displaying the true IAQ health level graph on a computing device of the individual.

In addition to one or more of the features described above, or as an alternative, further embodiments may include that the operations further include: transmitting the true IAQ health level graph to the computing device of the individual.

In addition to one or more of the features described above, or as an alternative, further embodiments may include that detecting the individual being located within the first room during the first time period of the plurality of time increments further includes: detecting wireless advertisement of a computing device of the individual using the first IAQ detector.

In addition to one or more of the features described above, or as an alternative, further embodiments may include that the wireless advertisement is a Bluetooth signal.

In addition to one or more of the features described above, or as an alternative, further embodiments may include that the first IAQ detector is located in a fire detector.

According to another embodiment, a computer program product tangibly embodied on a non-transitory computer readable medium is provided. The computer program product including instructions that, when executed by a processor, cause the processor to perform operations including: detecting a first IAQ data set within a first room at a plurality of time increments using a first IAQ detector in the first room; determining a first IAQ health level for each of the plurality of time increments based on the first IAQ data set; detecting a second IAQ data set within a second room at the plurality of time increments using a second IAQ detector in the second room; determining a second IAQ health level for each of the plurality of time increments based on the second IAQ data set; detecting an individual being located within the first room during a first time period of the plurality of time increments; detecting the individual being located within the second room during a second time period of the plurality of time increments; and extracting the first IAQ health level for each of the plurality of time increments during the first time period from the first IAQ health level for each of the plurality of time increments that was determined; extracting the second IAQ health level for each of the plurality of time increments during the second time period from the second IAQ health level for each of the plurality of time increments that was determined; and combining the first IAQ health level for each of the plurality of time increments during the first time period and the second IAQ health level for each of the plurality of time increments during the second time period into a true IAQ health level graph.

In addition to one or more of the features described above, or as an alternative, further embodiments may include that the operations further include: displaying the true IAQ health level graph on a computing device of the individual.

In addition to one or more of the features described above, or as an alternative, further embodiments may include that the operations further include: transmitting the true IAQ health level graph to the computing device of the individual.

In addition to one or more of the features described above, or as an alternative, further embodiments may include that detecting the individual being located within the first room during the first time period of the plurality of time increments further includes: detecting wireless advertisement of a computing device of the individual using the first IAQ detector.

In addition to one or more of the features described above, or as an alternative, further embodiments may include that the wireless advertisement is a Bluetooth signal.

In addition to one or more of the features described above, or as an alternative, further embodiments may include that the first IAQ detector is located in a fire detector.

Technical effects of embodiments of the present disclosure include monitor a location of an individual, tracking the IAQ in the location of the individual as they move from room-to-room, and then displaying on a computing device a true IAQ to the individual that they have experienced throughout the day.

The foregoing features and elements may be combined in various combinations without exclusivity, unless expressly indicated otherwise. These features and elements as well as the operation thereof will become more apparent in light of the following description and the accompanying drawings. It should be understood, however, that the following description and drawings are intended to be illustrative and explanatory in nature and non-limiting.

BRIEF DESCRIPTION OF THE DRAWINGS

The following descriptions should not be considered limiting in any way. With reference to the accompanying drawings, like elements are numbered alike:

FIG. 2 is a flow process illustrating a method of tracking an IAQ level experienced by an individual detector system is illustrated, according to an embodiment of the present disclosure.

DETAILED DESCRIPTION

Figure 1:
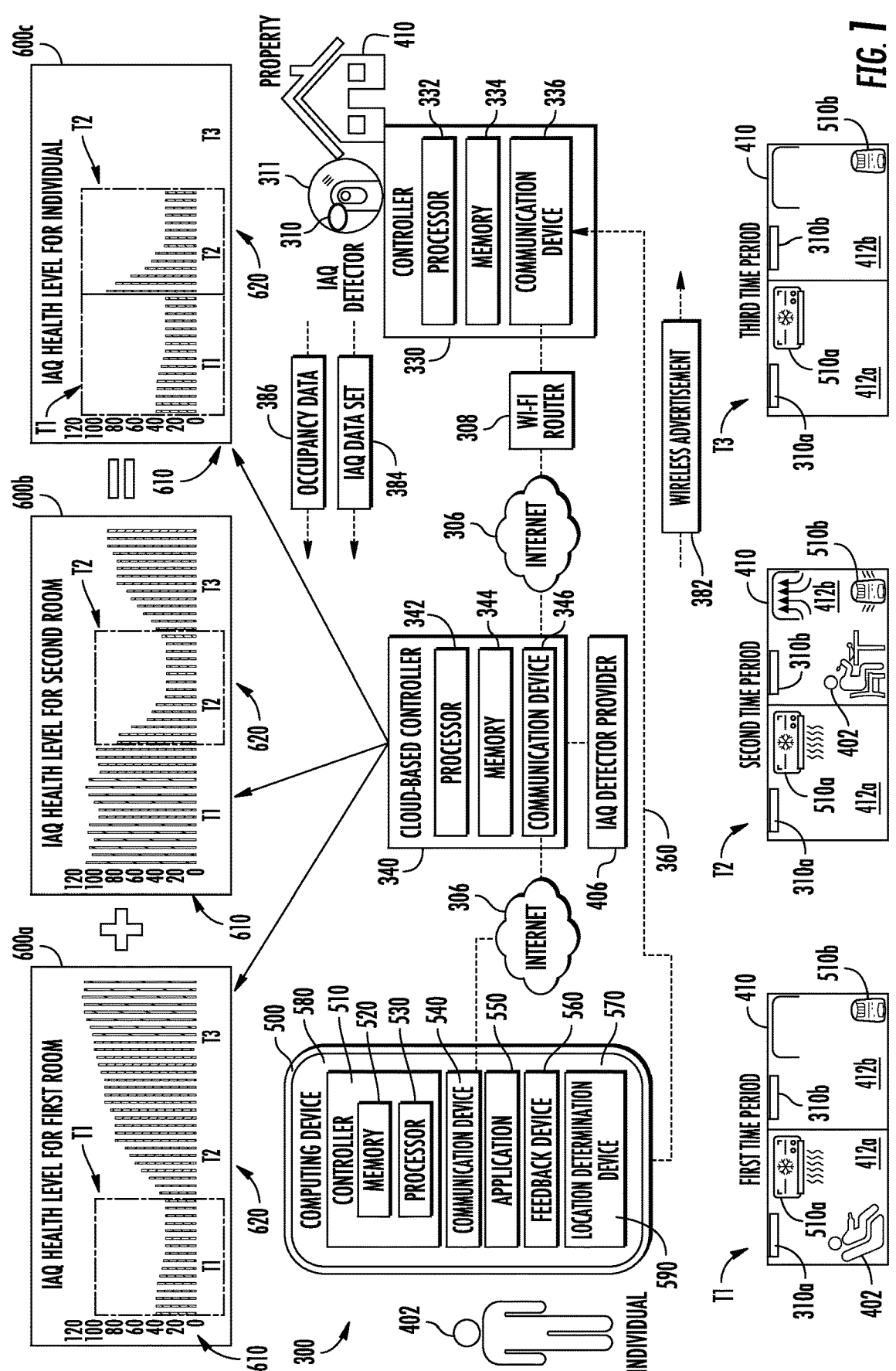
FIG. 1 is a schematic diagram of an indoor air quality (IAQ) detector system, according to an embodiment of the present disclosure.

A detailed description of one or more embodiments of the disclosed apparatus and method are presented herein by way of exemplification and not limitation with reference to the Figures.

The embodiments of the method and apparatus detailed herein relate to a method to show a true indoor air quality (IAQ) experienced by a user.

As aforementioned, IAQ is an important factor to create a safer indoor living environment. IAQ devices such as, air purifiers, air conditioners, humidifiers, dehumidifier, and ventilators are often used to control indoor air quality, but individuals are often given little feedback as to a resultant indoor air quality provided by these systems. IAQ may typically only be monitored in a single room at a time so it is impossible for an individual to monitor the exact air quality they experience throughout the course of a day as the individual moves from room-to-room.

Embodiments disclosed herein seek to monitor a location of an individual, tracking the IAQ in the location of the individual as they move from room-to-room, and then displaying on a computing device a true IAQ to the individual that they have experienced throughout the day.

Referring now to FIG. 1, a schematic diagram of an IAQ detector system 300 is illustrated, according to an embodiment of the present disclosure. It should be appreciated that, although particular systems are separately defined in the schematic block diagrams, each or any of the systems may be otherwise combined or separated via hardware and/or software.

The IAQ detector system 300 includes the cloud-based controller 340, an IAQ detector 310 and a computer application 550 installed or accessible to a computing device 500. The computer application 550 may be accessible from the computing device 500, such as, for example, a software-as-a service or a website. The computer application 550 may be in communication with the cloud database via the internet 306.

The IAQ detector 310 may be configured to detect an IAQ within the property 410. The IAQ detector 310 may be located within a fire detector 311 or may be the fire detector 311. The fire detector 311 may be a smoke detector, a $CO_2$ detector, a CO detector, a heat sensor, or any other IAQ detector known to one of skill in the art. The IAQ detector 310 and/or the fire detector may be an internet of things (IoT) connected device. The property 410 may be a home, an apartment, a garage, a room, a shed, a storage unit, a car, a vehicle, land, or any other area known to one of skill in the art that may need to be protected from fire. The property 410 may be owned by an individual 402, rented by the individual 402, in possession of an individual 402, in control of the individual 402, leased by the individual 402, or mortgaged by the individual 402. The individual 402 may be a person, an organization, a group, a partnership, a company, or a corporation.

The property 410 may have one or more IAQ detectors 310. The one or more IAQ detectors 310 may each be in communication with each other. In an embodiment there may be at least one IAQ detector 310 located in each room of the property 410. The property may include multiple rooms 412a, 412b. In the illustrated example of FIG. 1, the property 410 includes a first room 412a and a second room 412b.

The first room 412a includes a first IAQ detector 310a and a first IAQ device 510a. The first IAQ detector 310a is configured to detect an IAQ within the first room 412a. The first IAQ device 510a is configured to adjust an internal air quality within the first room 412a. The first IAQ device 510a may be an air purifier, an air conditioner, a humidifier, a dehumidifier, a ventilator, and/or any other IAQ device known to one of skill in the art.

The second room 412 b includes a second IAQ detector 310 b and a second IAQ device 510 b. The second IAQ detector 310 b is configured to detect an IAQ within the second room 412 b. The second IAQ device 510 b is configured to adjust an internal air quality within the second room 412 b. The second IAQ device 510 b may be an air purifier, an air conditioner, a humidifier, a dehumidifier, a ventilator and/or any other IAQ device known to one of skill in the art.

There may also be one or more IAQ devices 510 a, 510 b located in each room. The IAQ devices 510 a, 510 b may be the same or different across different rooms 412 a, 412 b.

IAQ detectors 310 may be used to simultaneously refer to the first IAQ detector 310 a and the second IAQ detector 310 b herein. It is understood that while two IAQ detectors 310 are described and illustrated herein, the embodiments disclosed herein may be applicable to one or more IAQ detectors 310 in a property 410.

The computing device 500 may be configured to emit a wireless advertisement 382. The wireless advertisement 382 may be Bluetooth, Bluetooth Low Energy, Ultra-wide band, or any other short range wireless signal known to one of skill in the art. The IAQ detector 310 may be configured to detect the wireless advertisement 382 of the computing device 500.

The computing device 500 may belong to or be in possession of an individual 402 of the property 410. Detection of the wireless advertisement 382 by the IAQ 310 would mean that the computing device 500 is within range of the IAQ detector 310, which would indicate that the computing device 500 and the individual 402 are in the same room as the IAQ detector 310. For example, if the first IAQ detector 310 a detects the wireless advertisement 382 then it would indicate that the individual 402 is within first room 412 a. For example, if the second IAQ detector 310 b detects the wireless advertisement 382 then it would indicate that the individual 402 is within second room 412 b.

Alternatively, at least one of the first IAQ detector 310 a or the second IAQ detector 310b may be configured to emit the wireless advertisement 382 and the computing device 500 may be configured to detect the wireless advertisement 382. Detection of the wireless advertisement 382 by the computing device 500 would mean that the computing device 500 is within range of the IAQ detector 310, which would indicate that the computing device 500 and the individual 402 are in the same room as the IAQ detector 310. For example, if the computing device 500 detects the wireless advertisement 382 of the first IAQ detector 310 a then it would indicate that the individual 402 is within first room 412 a. For example, if the computing device 500 detects the wireless advertisement 382 of the second IAQ detector 310 b then it would indicate that the individual 402 is within second room 412 b.

The IAQ detector 310 includes a controller 330 that is configured to communicate with the computer application 550 and the cloud-based controller 340. The controller 330 may be a controller dedicated solely for the IAQ detector 310 or shared with the fire detector 311. The controller 330 may be an electronic controller including a processor 332 and an associated memory 334 comprising computer-executable instructions (i.e., computer program product) that, when executed by the processor 332, cause the processor 332 to perform various operations. The processor 332 may be, but is not limited to, a single-processor or multi-processor system of any of a wide array of possible architectures, including field programmable gate array (FPGA), central processing unit (CPU), application specific integrated circuits (ASIC), digital signal processor (DSP) or graphics processing unit (GPU) hardware arranged homogenously or heterogeneously. The memory 334 may be but is not limited to a random access memory (RAM), read only memory (ROM), or other electronic, optical, magnetic or any other computer readable medium.

The controller 330 also includes a communication device 336. The communication device 336 may be capable of wireless communication including but not limited to Wi-Fi, Bluetooth, BLE, Ultra-Wideband, Zigbee, Z-Wave, Sub-GHz RF Channel, cellular, satellite, or any other wireless signal known to one of skill in the art. The communication device 336 may be configured to communicate with the cloud-based controller 340 through the internet 306. Alternatively, or additionally, the communication device 336 may be configured to communicate directly with the cloud-based controller 340. The communication device 336 may be configured to communicate with another IAQ detector 310a over a wired and/or wireless connection 311. The communication device 336 may be connected to the internet 306 through a Wi-Fi-router 308.

The cloud-based controller 340 may belong to and/or be managed by an IAQ detector provider 406, such as, for example a manufacturer of the IAQ detector 310 or an aftermarket support company for the IAQ detector 310.

The cloud-based controller 340 may perform a great deal of the analytics of the IAQ data set 384 and the occupancy data set 386 detected by the IAQ detector 310.

The cloud-based controller 340 may be a remote or local computer device that includes a processor 342 and an associated memory 344 comprising computer-executable instructions (i.e., computer program product) that, when executed by the processor 342, cause the processor 342 to perform various operations. The processor 342 may be, but is not limited to, a single-processor or multi-processor system of any of a wide array of possible architectures, including field programmable gate array (FPGA), central processing unit (CPU), application specific integrated circuits (ASIC), digital signal processor (DSP) or graphics processing unit (GPU) hardware arranged homogenously or heterogeneously. The memory 344 may be but is not limited to a random access memory (RAM), read only memory (ROM), or other electronic, optical, magnetic or any other computer readable medium.

The cloud-based controller 340 also includes a communication device 346. The communication device 346 may be capable of communication with the internet 306. The communication device 346 may be configured to communicate with the computing device 500 through the internet 306. The communication device 346 may be a software module that handles communications to-and-from the computer application 550 or to-and-from the controller 330.

The computing device 500 may be a desktop computer, a laptop computer, or a mobile computing device that is typically carried by a person, such as, for example a phone, a smart phone, a PDA, a smart watch, a tablet, a laptop, or any other mobile computing device known to one of skill in the art.

The computing device 500 includes a controller 510 configured to control operations of the computing device 500. The controller 510 may be an electronic controller including a processor 530 and an associated memory 520 comprising computer-executable instructions (i.e., computer program product) that, when executed by the processor 530, cause the processor 530 to perform various operations. The processor 530 may be, but is not limited to, a single-processor or multi-processor system of any of a wide array of possible architectures, including field programmable gate array (FPGA), central processing unit (CPU), application specific integrated circuits (ASIC), digital signal processor (DSP) or graphics processing unit (GPU) hardware arranged homogenously or heterogeneously. The memory 520 may be but is not limited to a random access memory (RAM), read only memory (ROM), or other electronic, optical, magnetic or any other computer readable medium.

The computing device 500 includes a communication device 540 configured to communicate with the internet 306 through one or more wireless signals. The one or more wireless signals may include Wi-Fi, Bluetooth, BLE, Ultra-Wideband, Zigbee, Z-Wave, Sub-GHz RF Channel, cellular, satellite, or any other wireless signal known to one of skill in the art. The computing device 500 is configured to communicate with the cloud-based controller 340 through the internet 306. Alternatively, the computing device 500 may be connected to the internet 306 through a hardwired connection. The computing device 500 may be configured to communicate directly with the IAQ detector 310 through a short-range wireless signal 360, including, but not limited to, Wi-Fi, Bluetooth, BLE, Ultra-Wideband, Zigbee, Z-Wave, Sub-GHz RF Channel, or any other wireless communication method known to one of skill in the art.

The computing device 500 may include a display device 580, such as for example a computer display, an LCD display, an LED display, an OLED display, a touchscreen of a smart phone, tablet, or any other similar display device known to one of the skill in the art. A user operating the computing device 500 is able to view the computer application 550 through the display device 580.

The computing device 500 includes an input device 570 configured to receive a manual input from a user (e.g., human being) of the computing device 500. The input device 570 may be a keyboard, a touch screen, a joystick, a knob, a touchpad, one or more physical buttons, a microphone configured to receive a voice command, a camera or sensor configured to receive a gesture command, an inertial measurement unit configured to detect a shake of the computing device 500, or any similar input device known to one of skill in the art. The user operating the computing device 500 is able to enter data into the computer application 550 through the input device 570. The input device 570 allows the user operating the computing device 500 to enter data into the computer application 550 via a manual input to input device 570. For example, the user may respond to a prompt on the display device 580 by entering a manual input via the input device 570. In one example, the manual input may be a touch on the touchscreen. In an embodiment, the display device 580 and the input device 570 may be combined into a single device, such as, for example, a touchscreen.

The computing device 500 may also include a feedback device 560. The feedback device 560 may activate in response to a manual input via the input device 570. The feedback device 560 may be a haptic feedback vibration device and/or a speaker emitting a sound. The feedback device 560 may activate to confirm that the manual input entered via the input device 570 was received via the computer application 550. For example, the feedback device 560 may activate by emitting an audible sound or vibrate the computing device 500 to confirm that the manual input entered via the input device 570 was received via the computer application 550.

The computing device 500 may also include a location determination device 590 that may be configured to determine a location of the computing device 500 using cellular signal triangulation, a global position satellite (GPS), or any location termination method known to one of skill in the art.

Each IAQ device 310 is configured to detect an IAQ data set 384 within the room 412a, 412b throughout the day. The IAQ data set 384 may be detected in real-time at a selected frequency. The IAQ data set 384 may be captured at a plurality of time increments throughout the day. The IAQ data set 384 may be various measurements of air quality including but not limited to, particulate levels, $CO_2$ levels, temperature, or any other IAQ parameter known to one of skill in the art. The IAQ data set 384 is then transmitted to the cloud-based controller 340 and the cloud-based controller 340 is configured to determine an IAQ health level 610 at each of the plurality of time increments 620 throughout the day based on the IAQ data set 384. The IAQ health level 610 may be a score of how healthy the air quality is within the room 412a, 412b. The IAQ health level 610 may be understood as the quality of the air experience by the individual 402.

The IAQ health level 610 may be specific to each IAQ detector 310 and thus may be specific to the room 412 a, 412 b where the IAQ detector is located and may be displayed as a graph. FIG. 1 illustrates an IAQ health level graph 600 a that displays the IAQ health level 610 detected within the first room 412 a at over the plurality of time increments 620. FIG. 1 illustrates an IAQ health level graph 600 b that displays the IAQ health level 610 detected within the second room 412 b at over the plurality of time increments 620. The IAQ health level graph 600 a, 600 b may be visible via the computing device 500.

The IAQ devices 510 a, 510 b may be programed to turn on when an individual 402 enters the room 412 a, 412 b or will soon be entering the room 412 a, 412 b and then shut off when the individual 402 leaves the room 412 a, 412 b. Thus, an IAQ health level 610 room may be allowed to degrade when an individual 402 leaves the room 412 a, 412 b as that individual 402 is not present. Therefore, looking at the IAQ health level 610 solely on a single room at a time basis may not give an accurate picture of the IAQ health level 610 experienced by an individual 402 as they come and go from the room 412 a, 412 b but rather it only gives an accurate picture of the IAQ health level 610 of that specific room.

The embodiment disclosed herein seek to rectify this problem by tracking the individual 402 as they move throughout the property 410 and combining IAQ health level 610 detected within each room 412a, 412b only while the individual was detected the room 412a, 412b.

Each IAQ detector 310 is configured to detect occupancy data 386 for a time period the individual 402 was located in a room 412a, 412b. The occupancy data 386 may be able to distinguish between different individuals 402 so that occupancy data 386 can be associated to a specific individual 402 and thus an IAQ health level 610 may also be associated with that specific individual 402.

In the example illustrated in FIG. 1, the individual 402 is detected by the first IAQ detector 310a to be in the first room 412a during a first time period T1, then the individual 402 is detected by the second IAQ detector 310b to be in the second room 412b during a second time period T2, and then the individual 402 is detected by neither the first IAQ detector 310a nor the second detector 310b and is believed to have left the property 410 during a third time period T3.

The cloud based controller 340 is then configured to combine the IAQ health level 610 for the first room 412a during the first time period T1 and the IAQ health level 610 for the second room 412b during the second time period T1 into a true IAQ health level graph 600c that only shows the IAQ heath level 610 experienced by the individual 402. Advantageously, by only showing the IAQ heath level 610 experienced by the individual 402, then the individual 402 has a better understanding of their own health over the course of the plurality of time increments 620. The true IAQ health level graph 600c may be accessible to the individual 402 through the computing device 500, wherein the true IAQ health level graph 600c may be displayed on the computing device 500.

Referring to FIG. 2, within continued references to FIGS. 1-2, a flow diagram illustrating a method 800 of tracking an IAQ level 610 experienced by an individual 402 using detector system 300 is illustrated, in accordance with an embodiment of the present disclosure. In an embodiment, the method 800 may be performed by the cloud-based controller 340.

At block 804, a first IAQ data set 384 within a first room 412a is detected at a plurality of time increments 620 using a first IAQ detector 310a in the first room 412a.

At block 806, a first IAQ health level 610 is determined for each of the plurality of time increments 620 based on the first IAQ data.

At block 808, a second IAQ data set 384 within a second room 412b is detected at the plurality of time increments 620 using a second IAQ detector 310b in the second room 412b.

At block 810, a second IAQ health level 610 is determined for each of the plurality of time increments 620 based on the second IAQ data.

At block 812, an individual 402 being located within the first room 412a during a first time period T1 of the plurality of time increments 620 is detected.

At block 814, the individual 402 being located within the second room 412 b during a second time period T2 of the plurality of time increments 620 is detected.

At block 816, the first IAQ health level 610 is extracted for each of the plurality of time increments 620 during the first time period T1 from the first IAQ health level 610 for each of the plurality of time increments 620 that was determined.

At block 818, the second IAQ health level 610 is extracted for each of the plurality of time increments 620 during the second time period T2 from the second IAQ health level 610 for each of the plurality of time increments 620 that was determined.

At block 820, the first IAQ health level 610 for each of the plurality of time increments 620 during the first time period T1 and the second IAQ health level 610 for each of the plurality of time increments 620 during the second time period T2 are combined into a true IAQ health level graph 600c.

The method 800 may further include that the true IAQ health level graph 600c is displayed on a computing device 500 of the individual 402. The method 800 may also include that the true IAQ health level graph 600c is transmitted to the computing device 500 of the individual 402.

The individual 402 being located within the first room 412a during the first time period T1 of the plurality of time increments 620 may be detected by detecting wireless advertisement 382 of a computing device 500 of the individual 402 using the first IAQ detector 310a. The wireless advertisement 382 may be a Bluetooth signal. The first IAQ detector 310a may be located in a fire detector 311 as aforementioned.

While the above description has described the flow process of FIG. 2 in a particular order, it should be appreciated that unless otherwise specifically required in the attached claims, the ordering of the steps may be varied.

The term "about" is intended to include the degree of error associated with measurement of the particular quantity based upon the equipment available at the time of filing the application. For example, "about" can include a range of ±8% or 5%, or 2% of a given value.

The terminology used herein is for the purpose of describing particular embodiments only and is not intended to be limiting of the present disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, element components, and/or groups thereof.

While the present disclosure has been described with reference to an exemplary embodiment or embodiments, it will be understood by those skilled in the art that various changes may be made and equivalents may be substituted for elements thereof without departing from the scope of the present disclosure. In addition, many modifications may be made to adapt a particular situation or material to the teachings of the present disclosure without departing from the essential scope thereof. Therefore, it is intended that the present disclosure not be limited to the particular embodiment disclosed as the best mode contemplated for carrying out this present disclosure, but that the present disclosure will include all embodiments falling within the scope of the claims.

What is claimed is:

1. A method of tracking an indoor air quality (IAQ) level experienced by an individual, the method comprising:
   detecting a first IAQ data set within a first room at a plurality of time increments using a first IAQ detector in the first room;
   determining a first IAQ health level for each of the plurality of time increments based on the first IAQ data set;
   detecting a second IAQ data set within a second room at the plurality of time increments using a second IAQ detector in the second room;
   determining a second IAQ health level for each of the plurality of time increments based on the second IAQ data set;
   detecting the individual being located within the first room during a first time period of the plurality of time increments;
   detecting the individual being located within the second room during a second time period of the plurality of time increments;

extracting the first IAQ health level for each of the plurality of time increments during the first time period from the first IAQ health level for each of the plurality of time increments that was determined;

extracting the second IAQ health level for each of the plurality of time increments during the second time period from the second IAQ health level for each of the plurality of time increments that was determined; and combining the first IAQ health level for each of the plurality of time increments during the first time period and the second IAQ health level for each of the plurality of time increments during the second time period into a true IAQ health level graph.

2. The method of claim 1, further comprising: displaying the true IAQ health level graph on a computing device of the individual.

3. The method of claim 2, further comprising: transmitting the true IAQ health level graph to the computing device of the individual.

4. The method of claim 1, wherein detecting the individual being located within the first room during the first time period of the plurality of time increments further comprises:

detecting wireless communication of a computing device of the individual using the first IAQ detector.

5. The method of claim 4, wherein the wireless communication is a Bluetooth signal.

6. The method of claim 1, wherein the first IAQ detector is located in a fire detector.

7. An indoor air quality (IAQ) detector system having one or more IAQ detectors, the IAQ detector system comprising:

a processor; and a memory comprising computer-executable instructions that, when executed by the processor, cause the processor to perform operations, the operations comprising:

detecting a first IAQ data set within a first room at a plurality of time increments using a first IAQ detector in the first room;

determining a first IAQ health level for each of the plurality of time increments based on the first IAQ data set;

detecting a second IAQ data set within a second room at the plurality of time increments using a second IAQ detector in the second room;

determining a second IAQ health level for each of the plurality of time increments based on the second IAQ data set;

detecting an individual being located within the first room during a first time period of the plurality of time increments;

detecting the individual being located within the second room during a second time period of the plurality of time increments;

extracting the first IAQ health level for each of the plurality of time increments during the first time period from the first IAQ health level for each of the plurality of time increments that was determined;

extracting the second IAQ health level for each of the plurality of time increments during the second time period from the second IAQ health level for each of the plurality of time increments that was determined; and combining the first IAQ health level for each of the plurality of time increments during the first time period and the second IAQ health level for each of the plurality of time increments during the second time period into a true IAQ health level graph.

8. The IAQ detector system of claim 7, wherein the operations further comprise: displaying the true IAQ health level graph on a computing device of the individual.

9. The IAQ detector system of claim 8, wherein the operations further comprise: transmitting the true IAQ health level graph to the computing device of the individual.

10. The IAQ detector system of claim 7, wherein detecting the individual being located within the first room during the first time period of the plurality of time increments further comprises:

detecting wireless communication of a computing device of the individual using the first IAQ detector.

11. The IAQ detector system of claim 10, wherein the wireless communication is a Bluetooth signal.

12. The IAQ detector system of claim 7, wherein the first IAQ detector is located in a fire detector.

13. The IAQ detector system of claim 7, wherein the first IAQ detector detects one or more of particulate levels and carbon dioxide ($CO_2$) levels.

14. A non-transitory computer program product tangibly embodied on a non-transitory computer readable medium, the non-transitory computer program product including instructions that, when executed by a processor, cause the processor to perform operations comprising:

detecting a first IAQ data set within a first room at a plurality of time increments using a first IAQ detector in the first room;

determining a first IAQ health level for each of the plurality of time increments based on the first IAQ data set;

detecting a second IAQ data set within a second room at the plurality of time increments using a second IAQ detector in the second room;

determining a second IAQ health level for each of the plurality of time increments based on the second IAQ data set;

detecting an individual being located within the first room during a first time period of the plurality of time increments;

detecting the individual being located within the second room during a second time period of the plurality of time increments;

extracting the first IAQ health level for each of the plurality of time increments during the first time period from the first IAQ health level for each of the plurality of time increments that was determined;

extracting the second IAQ health level for each of the plurality of time increments during the second time period from the second IAQ health level for each of the plurality of time increments that was determined; and combining the first IAQ health level for each of the plurality of time increments during the first time period and the second IAQ health level for each of the plurality of time increments during the second time period into a true IAQ health level graph.

15. The non-transitory computer program product of claim 14, wherein the operations further comprise: displaying the true IAQ health level graph on a computing device of the individual.

16. The non-transitory computer program product of claim 15, wherein the operations further comprise: transmitting the true IAQ health level graph to the computing device of the individual.

17. The non-transitory computer program product of claim 14, wherein detecting the individual being located within the first room during the first time period of the plurality of time increments further comprises:

detecting wireless communication of a computing device of the individual using the first IAQ detector.

18. The non-transitory computer program product of claim 17, wherein the wireless communication is a Bluetooth signal.

19. The non-transitory computer program product of claim 14, wherein the first IAQ detector is located in a fire detector.

\* \* \* \* \*